(12) United States Patent
Jones

(10) Patent No.: US 10,791,997 B2
(45) Date of Patent: Oct. 6, 2020

(54) METHOD AND SYSTEM FOR AN OMNIDIRECTIONAL PULL-CORD SENSOR ASSEMBLY

(71) Applicant: CareHawk Inc., Kitchener (CA)

(72) Inventor: Nicolas Jones, Kitchener (CA)

(73) Assignee: CAREHAWK INC., Kitchener, Ontario (CA)

( * ) Notice: Subject to any disclaimer, the term of this patent is extended or adjusted under 35 U.S.C. 154(b) by 134 days.

(21) Appl. No.: 15/871,496

(22) Filed: Jan. 15, 2018

(65) Prior Publication Data
US 2018/0199896 A1 Jul. 19, 2018

Related U.S. Application Data

(60) Provisional application No. 62/446,107, filed on Jan. 13, 2017.

(51) Int. Cl.
| | | |
|---|---|---|
| *G01B 7/14* | (2006.01) | |
| *A61B 5/00* | (2006.01) | |
| *H03K 17/97* | (2006.01) | |
| *G01R 33/00* | (2006.01) | |
| *H01H 3/02* | (2006.01) | |

(52) U.S. Cl.
CPC .......... *A61B 5/747* (2013.01); *G01R 33/0005* (2013.01); *G01R 33/0047* (2013.01); *H01H 3/0226* (2013.01); *H03K 17/97* (2013.01); *H01H 2003/0233* (2013.01)

(58) Field of Classification Search
CPC ............ G01R 33/0005; G01R 33/0052; G01R 33/0047; G01R 33/09; G01R 33/093; G01R 33/0206; G01R 33/06; G01R 33/063; G01R 33/18; G01R 15/207; G01D 5/145; G01D 5/147; G01D 5/247; G01B 7/003; G01B 7/30; A61B 5/747; A63B 21/00192; A63B 21/018; A63B 21/0051; A63B 21/16; A63B 21/4007; A63B 21/4009; A63B 21/4011; A63B 21/4025; A63B 21/4043; H01H 3/0226; H01H 2003/0233
See application file for complete search history.

(56) References Cited

U.S. PATENT DOCUMENTS

| | | | |
|---|---|---|---|
| 3,992,938 A * | 11/1976 | Miller | G07D 5/08 73/163 |
| 4,728,928 A * | 3/1988 | Shipley | G08B 25/12 340/287 |
| 5,867,877 A | 2/1999 | Patterson et al. | |

(Continued)

OTHER PUBLICATIONS

Canadian Intellectual Property Office as International Searching Authority, International Search Report for PCT/CA2018/050036, dated Apr. 5, 2018.

(Continued)

*Primary Examiner* — Thang X Le
(74) *Attorney, Agent, or Firm* — Gowling WLG (Canada) LLP; Jeffrey W. Wong (57) ABSTRACT

The disclosure is directed at a method and system for a pull-cord sensor assembly that includes an activation portion including a magnet portion for generating a magnetic field; a sensor portion for sensing a level of the magnetic field level; a comparator for comparing the level of the magnetic field with a threshold value; and a pull cord integrated with the activation portion.

20 Claims, 8 Drawing Sheets

(56) References Cited

U.S. PATENT DOCUMENTS

| | | | |
|---|---|---|---|
| 6,457,896 B1 | 10/2002 | deDoes | |
| 6,671,933 B1* | 1/2004 | Friend | F16B 45/04 24/115 F |
| 2003/0079977 A1* | 5/2003 | Wei | H03K 17/96 200/331 |
| 2003/0136443 A1* | 7/2003 | Wain | B60N 2/0224 137/38 |
| 2009/0027044 A1* | 1/2009 | Hornung | G01D 5/06 324/207.2 |
| 2009/0033492 A1* | 2/2009 | Rapp | G08B 13/1445 340/568.8 |
| 2014/0320114 A1* | 10/2014 | Enkovaara | G05B 19/042 324/207.11 |

OTHER PUBLICATIONS

Canadian Intellectual Property Office as International Searching Authority, International Preliminary Report on Patentability for PCT/CA2018/050036, dated Jul. 16, 2019.

* cited by examiner

METHOD AND SYSTEM FOR AN OMNIDIRECTIONAL PULL-CORD SENSOR ASSEMBLY

CROSS-REFERENCE TO OTHER APPLICATIONS

The application claims priority from U.S. Provisional Application No. 62/446,107 dated Jan. 13, 2017 which is hereby incorporated by reference.

FIELD OF THE DISCLOSURE

The present disclosure relates generally to manually activated sensors utilized in signalling devices. More specifically, the present disclosure relates to a method and system for an omnidirectional pull-cord sensor.

BACKGROUND OF THE DISCLOSURE

In certain care facilities, such as hospital, nursing homes or assisted living facilities, when a problem arises, the patients or residents may not be able to signal such a problem to other individuals, such as staff, nurses, attendants, that are in the facility. As such, safeguards are installed in these facilities to assist the residents when an emergency or problem occurs. These safeguards may be seen as signalling devices or systems.

Currently, a variety of signalling systems utilize manually activated sensors as a way for a resident to trigger a signalling operation. Commonly utilized sensors include pushbutton switches and/or pull-cords sensors. Pull-cord sensors are commonly utilized in lavatories and shower areas of care facilities where the resident may fall whereby it is desirable to have a signalling apparatus that is within reach from the floor for the fallen resident. The sensors may also be implemented in locations where the resident may be sitting and/or standing.

Within the lavatories and shower areas, the sensors are frequently subject to high humidity and water exposure whereby water or water vapour may damage the components of the sensors. Furthermore, some pull-cord systems may present a hazard if the resident, either intentionally or unintentionally, becomes entangled with the cord. In some systems, a break-away feature in implemented to reduce or minimize the likelihood that an individual suffers serious injury as a result of entanglement.

Furthermore, pull-cord sensors typically include mechanical switches. These mechanical switches tend to have a limited operational life. In particular, electrical contacts within the switches are regularly subject to contamination, fretting, and/or corrosion. Moreover, mechanical switches can be subject to false indications when exposed to vibration and mechanical shock. Consequently, pull-cord sensors based on mechanical switches tend to be designed to require a relatively high activation pull force in order to have an adequate immunity from false indications. However, a high activation pull-cord force may be problematic, particularly for residents that have limited arm/hand mobility and/or strength.

Some current pull-cords systems are also subject to a problem for infection control in that the cord is relatively time consuming to clean. In some scenarios, the cord may be difficult to clean completely given that, in certain current systems, the cord, or a portion thereof, remains attached to the signalling device.

Therefore, there is provided a novel method and system for an omnidirectional pull-cord sensor that overcomes some of the disadvantages of the current pull-cord systems.

SUMMARY OF THE DISCLOSURE

In its broad aspect, the present disclosure is directed at a method and system for an omnidirectional pull-cord sensor. In one embodiment, the disclosure provides a pull-cord sensor utilizing a solid-state magnetic field detector, a permanent magnet housed in an elastomeric body that is not subject to mechanical wear, is highly immune to false indications due to shock and/or vibration, and incorporates a cord break-away feature where the entire cord assembly detaches from the signalling device.

In another aspect, the cord break-away feature is adapted to provide an apparatus to easily detach and reattach a cord assembly for, among other purposes, cleaning, sterilization by immersion in disinfectant and/or replacement. In another aspect, the disclosure provides a pull-cord sensor with a very low activation pull force independent of the direction of application of the pull force. In another aspect, the disclosure provides a pull-cord sensor that is inherently sealed providing little or no path for water or water vapor ingress.

In one aspect, there is provided a pull-cord sensor assembly including an activation portion including a magnet portion for generating a magnetic field; a sensor portion for sensing a level of the magnetic field level; a comparator for comparing the sensed level of the magnetic field with a threshold value; and a pull cord integrated with the activation portion.

In another embodiment, the activation portion further includes a pull-cord coupler; and a plate portion having a central portion, the central portion integrated with the pull-cord coupler. In a further embodiment, the pull-cord coupler and the plate portion are a single piece. In yet another embodiment, the pull-cord coupler includes a tip portion; a rib portion; a ramp portion connecting the tip portion to the rib portion whereby a diameter of the trip portion is less than a diameter of the rib portion; and a ring portion connected to the rib portion. In another embodiment, the pull-cord is integrated with the activation portion via the ring portion. In another embodiment, the central portion includes an annular housing portion defined by an annular wall for housing the pull-cord coupler; and an opening at one end of the central portion for receiving the pull-cord coupler; wherein a diameter of the opening is smaller than a diameter of the annular housing and wherein the magnet is located at an end of the central portion opposite the opening. In yet a further embodiment, the annular housing portion includes an annular ridge.

In another embodiment, the assembly further includes a substrate portion wherein the activation portion is mounted on one side of the substrate portion and the sensor portion is mounted on another side of the substrate opposite the activation portion. In one embodiment, the sensor portion is mounted directly opposite the magnet portion. In another embodiment, the substrate portion is a printed circuit board. In yet another embodiment, the sensor portion is mounted adjacent the magnet portion.

In a further embodiment, the plate portion includes at least one annular ring surrounding the central portion enabling flexibility of the central portion. In another embodiment, the plate portion is made from an elastomeric material. In yet another embodiment, the pull cord includes a handle at an end of the pull cord opposite the activation portion. In a further embodiment, the comparator is a processor or an electronic circuit. In another embodiment, the comparator is integrated with the sensor portion.

BRIEF DESCRIPTION OF THE DRAWINGS

Embodiments of the present disclosure will now be described, by way of example only, with reference to the attached Figures.

FIG. 2b is a side view of the plate of FIG. 2a;

FIG. 2c is a front view of the plate of FIG. 2a;

FIG. 2d is a top view of the plate of FIG. 2a;

FIG. 16b is a second cross-sectional view of the embodiment of FIG. 16a; and

FIG. 17b is a second cross-sectional view of the embodiment of FIG. 17a; and

DETAILED DESCRIPTION

The disclosure is directed at a method and system for an omnidirectional pull-cord sensor assembly. In one embodiment, the disclosure is directed at a sensor assembly whereby the pull-cord can be pulled in any direction (i.e. omnidirectional) in order to activate a signal, or alarm and the like. In one embodiment, the present disclosure may be used as part of a nurse-call system.

In one embodiment, the system includes a magnetic field sensor that senses a magnetic field that is generated by a magnet. When the magnetic field sensor fails to sense a predetermined magnetic field threshold level, an alarm or signal is activated by the system.

Figure 1:
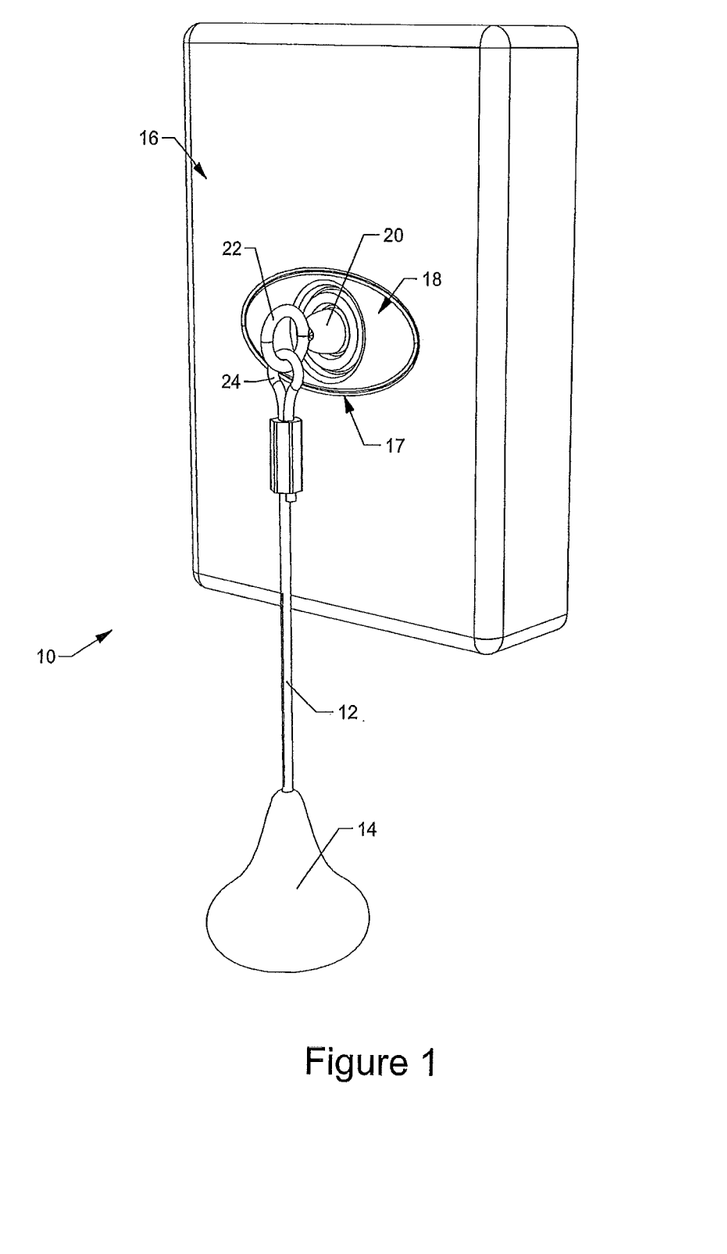
FIG. 1 is a perspective view of a pull-cord sensor assembly integrated within a call station.

Turning to FIG. 1, a perspective view of a pull-cord sensor assembly attached to a call station is shown. The pull-cord sensor assembly 10 includes a pull-cord 12 with a handle, or knob, 14 at one end. The handle 14 provides an area for an individual to grip the pull-cord in order to pull the cord to activate a sensor (not shown) within the call station 16. The pull-cord sensor assembly 10 further includes an activation portion 17 including a magnet (not shown) and a plate portion 18 that is integrated within the call station 16. In the current embodiment, the plate portion 18 is made from an elastomeric material, such as, but not limited to, silicone. The plate portion 18 includes a central portion 20 for receiving an attachment mechanism 22, such as a pull-cord coupler, that is connected to the pull-cord 12. In the current embodiment, the pull-cord coupler 22 is ring-shaped and connected to a loop 24 at the end of the pull-cord 12. It will be understood that other ways to connect the pull-cord 12 with the attachment mechanism, may be contemplated. The pull-cord assembly 10, or activation portion, further includes a sensor assembly (as will be described below) within the call station 16 to sense when the pull-cord 12 has been pulled in order to activate the necessary signal or alarm. In a preferred embodiment, the pull-cord assembly 10 includes a break-away feature that allows the cord to "break-away" from the call station 16, such as required in some patient care facilities.

Figure 2A:
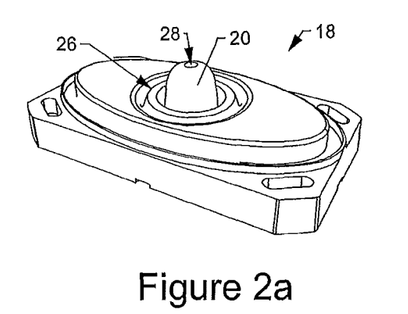
FIG. 2a is a perspective view of a plate portion of a pull-cord sensor assembly.
Figure 2B:
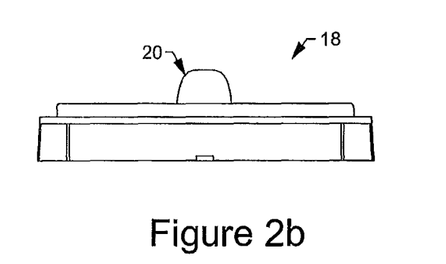
Figure 2C:
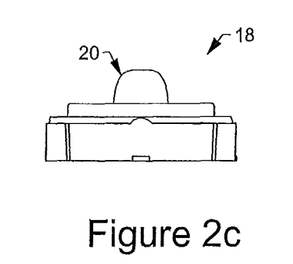
Figure 2D:
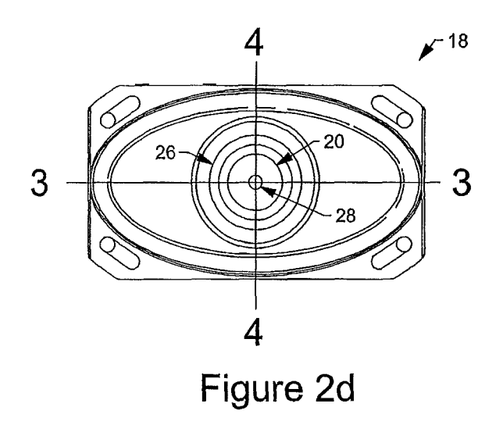

Turning to FIGS. 2a to 2d, various views of the plate portion 18 are shown. FIG. 2a is a perspective view, FIG. 2b is a front view, FIG. 2c is a side view of the plate and FIG. 2d is a top view of the plate portion. The plate portion 18 includes the central portion 20 flexibly supported by annular rings 26 to support movement of the central portion 20 away from the call station 16 when the pull-cord 12 is pulled. The central portion 20 further includes a hole 28 for receiving an end of the attachment mechanism 22.

Figure 3:
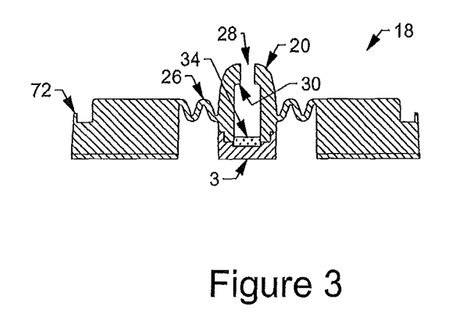
FIG. 3 is a cross-section view taken along points 3-3 of FIG. 2d.
Figure 4:
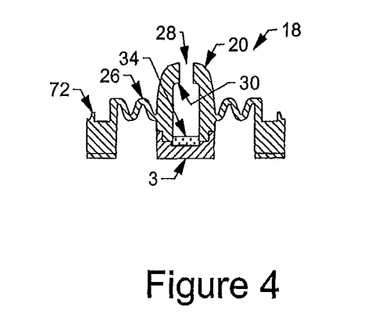
FIG. 4 is a cross-section view taken along points 4-4 of FIG. 2d.

Turning to FIG. 3, a cross-sectional view taken along line 3-3 of FIG. 2d is provided. FIG. 4 is a cross-sectional view taken along line 4-4 of FIG. 2d. As shown in these Figures, the central portion 20 further includes an annular ridge 30 on its inner surface to define an attachment mechanism receiving area 32 within which an end of the attachment mechanism 22 resides. As can be seen, the diameter of the hole 28 is smaller than the diameter of the attachment mechanism receiving area 32. The pull-cord sensor assembly 10, or activation portion further includes a magnet 34 located at a bottom of the attachment mechanism receiving area 32. The magnet 34 is preferably a permanent magnet having a predetermined field strength that is suitable for sensing by a sensor. In the current embodiment, the magnet 34 is affixed with a cap 36 to the central portion 20 preferably by an adhesive or similar material. The cap 36 provides a continuous elastomeric membrane that may be impervious to liquids and water vapor to prevent or reduce the likelihood of liquids and/or water vapor damaging components of the pull-cord sensor assembly 10. The plate portion 18 further includes an oval tab or ridge 72.

As can be seen in FIGS. 3 and 4, in the current embodiment, the central portion 20 and annular rings 26 are substantially radially symmetrical and equivalent.

Figure 5:
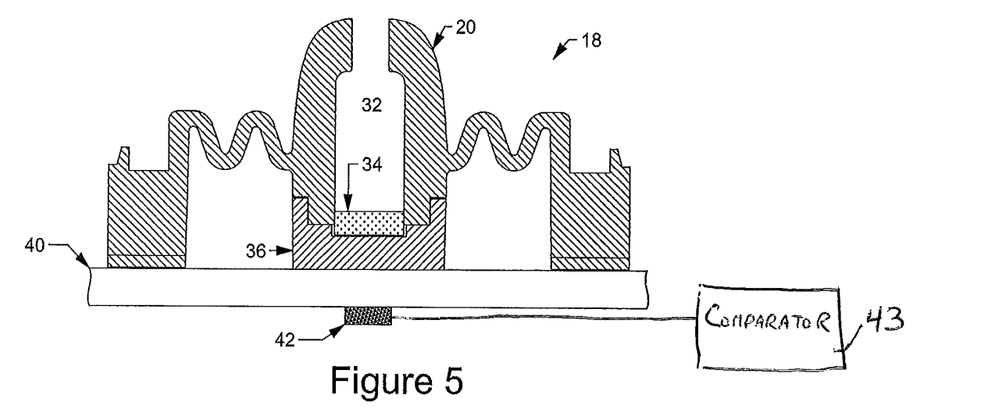
FIG. 5 is the cross-section of FIG. 3 mounted on a substrate and sensor.

Referring now to FIG. 5, a cross-sectional view of the plate portion mounted to a substrate is shown. In FIG. 5, the pull-cord sensor assembly 10 is positioned adjacent, or mounted, to a substrate 40. A sensor 42 is mounted to a side of the substrate 40 opposite the plate portion 18. In one embodiment, the substrate 40 can be a flat piece of metal, a flat piece of plastic or a printed circuit board. In the preferred embodiment, the sensor 42 is mounted directly opposite the magnet 34. The sensor 42 senses the presence of the magnetic field generated by the magnet and when the magnetic field is removed, the sensor determines that the pull-cord has been pulled and performs the necessary actions to generate the signal or the alarm, as required. The sensor 42 may be an analog or digital sensor.

Figure 6:
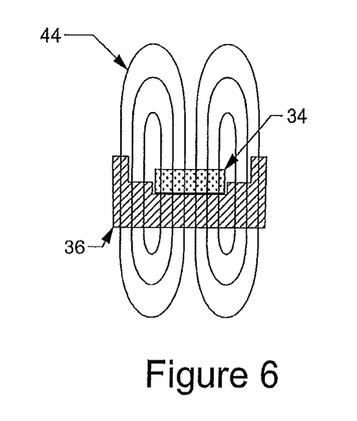
FIG. 6 is a schematic view of a magnetic field generated by a magnet of the pull-cord sensor assembly.
Figure 7:
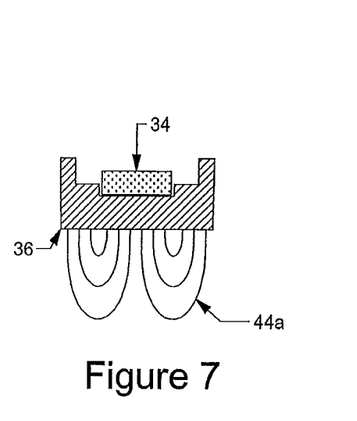
FIG. 7 is a schematic view of a portion of the magnetic field that extends through a lower portion of the pull-cord sensor assembly.

FIGS. 6 and 7 are schematic diagrams reflecting an example of how the magnetic field may be generated by the magnet. In the current embodiment, the permanent magnet 34 generates a magnetic field (represented by lines 44). It will be understood, that the lines are for illustration purposes and that the magnetic field extends essentially indefinitely in all directions, however, it may be considered for practical purposes to have limited dimensions when considering a predetermined minimum field strength. In FIG. 7, a bottom portion of the magnetic lines 44a representing the portion of the magnetic field that extends though the cap 36 and exceeds a predetermined minimum field strength are shown.

Figure 8:
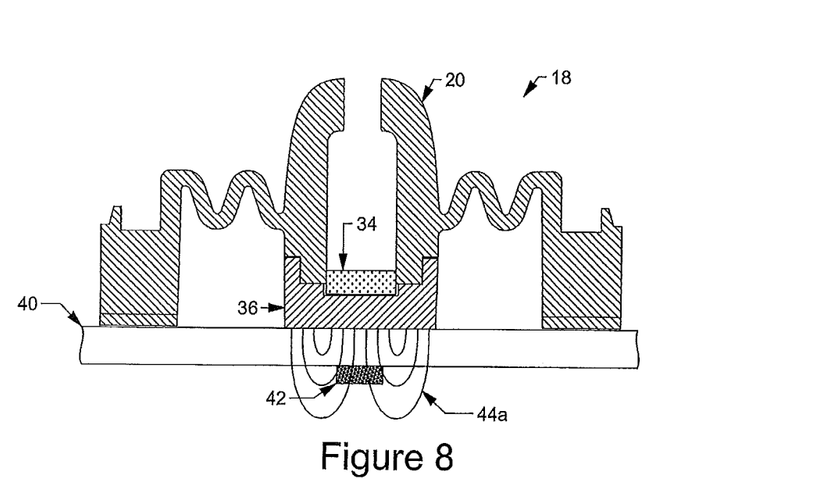
FIG. 8 is a cross-section of FIG. 5 with lines reflecting the magnetic field generated by the magnet of the pull-cord sensor assembly.

Referring now to FIG. 8, the lower portion of the magnetic lines 44a are superimposed on FIG. 5. As can be seen, the magnetic lines 44a transect magnetic sensor 42 substantially perpendicular to substrate 40. Therefore, when the plate portion 18 is in the rest position (or not activated position), the magnetic sensor 42 senses the presence of the magnetic field generated by the magnet 34. The threshold level of the magnetic field that the sensor 42 needs to sense before activating the signal can be pre-programmed or determined by the type of sensor used. In an alternative embodiment, the system may further include a comparator 43 for comparing the sensed magnetic field level with the threshold level to determine if the sensed level meets the threshold. In one embodiment, the comparator may be a processor that is performing the comparison via a module. In another embodiment, the comparator may be an electronic circuit or a component integrated within the sensor. In a preferred embodiment, the sensor 42 is preferably selected to be sensitive to magnetic fields perpendicular to its mounting axis, resulting in the maximum or a high sensed field strength in the configuration of FIG. 8.

In one embodiment, magnetic sensor 42 may produce an output voltage or digital value proportional to the sensed magnetic field strength, or could produce a detection signal resulting from a comparison of a sensed magnetic field strength to a predetermined threshold. It will be further understood that should magnetic sensor 42 have a proportional output, an electronic circuit may be employed to compare the proportional output to a predetermined limit and produce an equivalent to the detection signal. Although not shown, the system may include a processor for receiving the detection signal from the sensor or from other circuitry and then perform the necessary actions to generate an alarm or signal.

Figure 9:
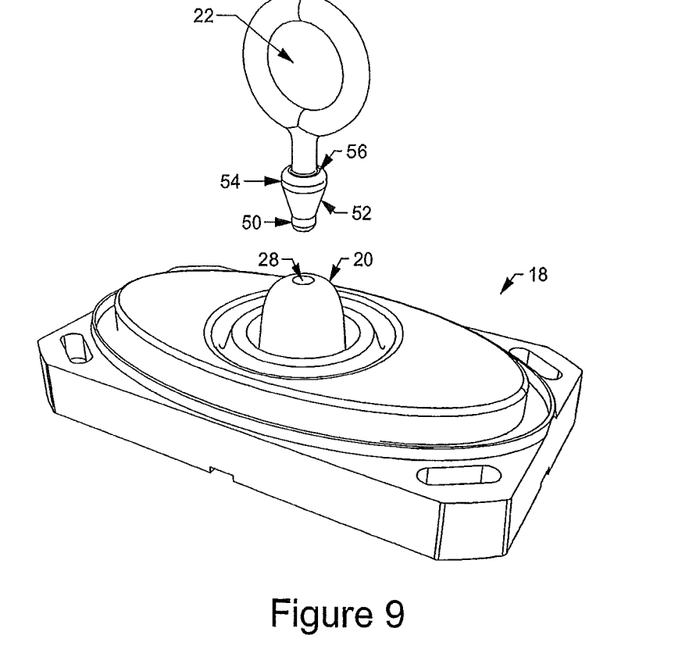
FIG. 9 is a perspective view of the plate portion and a pull-cord coupler.
Figure 10:
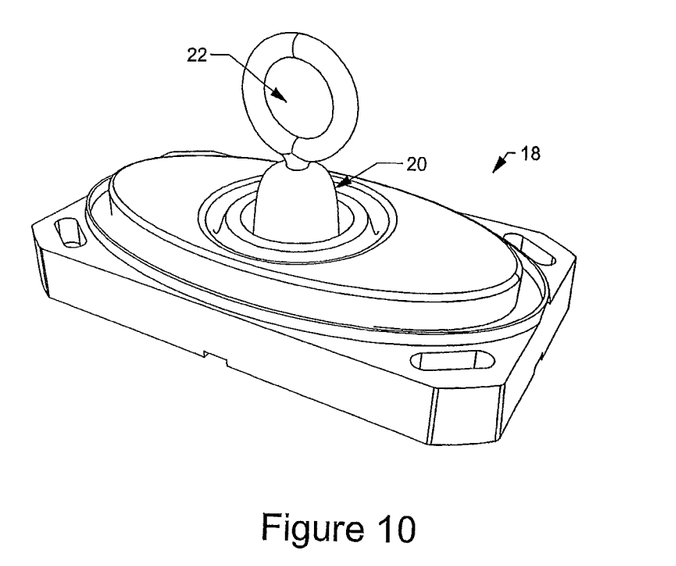
FIG. 10 is a perspective view of the plate portion with the pull-cord coupler inserted within the plate portion.

Turning to FIGS. 9 and 10, perspective views of an activation portion separated from the central portion and an activation portion inserted in the central portion are provided. Referring now to FIG. 9, the attachment portion 22, which can be seen as the pull-cord coupler, is depicted positioned to be inserted into the hole 28 of central portion 20. A tip 50 of the pull-cord coupler is approximately the same diameter as hole 28, with a ramp portion 52 gradually increasing the diameter to a rib portion 54. At a boundary of rib portion 54, the diameter is reduced to the diameter of tip 50 creating an edge area 56.

With reference to FIG. 10, showing the activation portion inserted into hole 28, the pull-cord coupler 22 is retained in place by edge 56 resting against the annular ridge 30 (as shown in FIG. 3) inside the hole 28. The is more clearly shown in FIGS. 11 to 13.

Figure 11A:
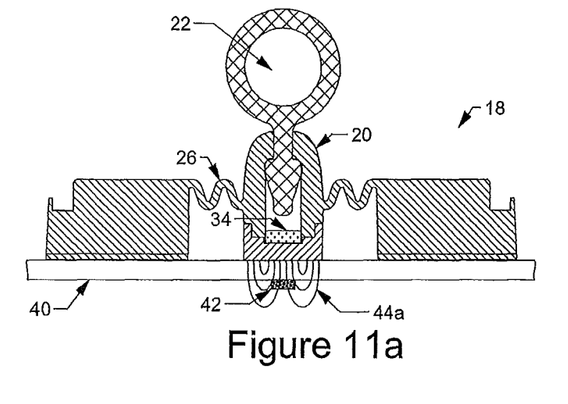
FIG. 11a is a cross-sectional view of the plate portion and pull-cord coupler of FIG. 10 in an at-rest position with magnetic field lines.
Figure 11B:
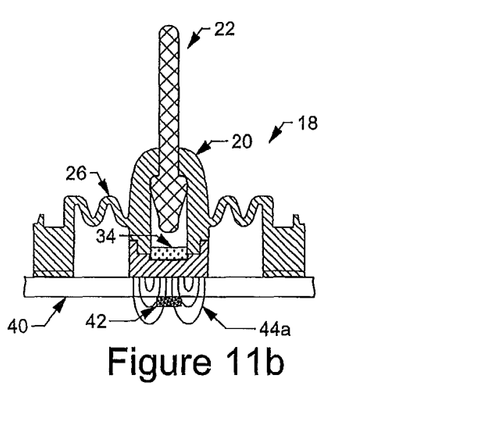
FIG. 11b is a second cross-sectional view of the plate portion and pull-cord coupler of FIG. 10 in an at-rest position with magnetic field lines.

Referring now to FIGS. 11a and 11b, cross-sectional views of the pull-cord sensor assembly in an at rest position are shown. As can be seen, based on the position of the magnet 34 with respect to the sensor 42, it can be seen that the field strength sensed by magnetic sensor 42 is strong, or high, since the distance between the magnet 34 and the sensor is low or at a minimum distance and magnetic lines 44a transect the magnetic sensor 42 essentially in line with its maximum or highest sensitivity orientation. As described above, a pull-cord (not shown) is typically attached to the attachment portion 22, however, it will be understood that the nature of attachment and type of pull-cord is not material to the present disclosure.

Figure 12A:
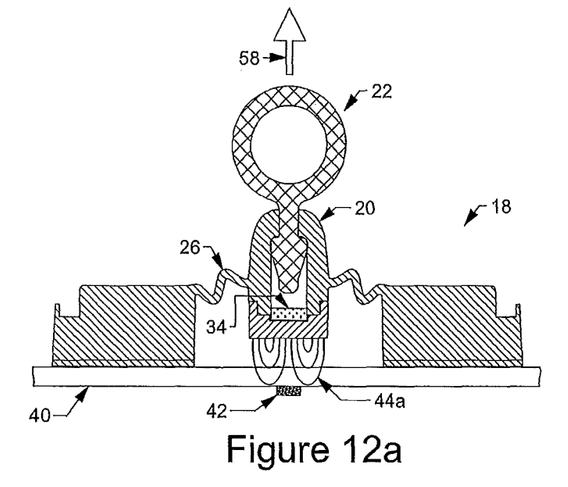
FIG. 12a is a cross-sectional view of the plate portion and pull-cord coupler of FIG. 10 in an intermediate, or distorted, position with magnetic field lines.
Figure 12B:
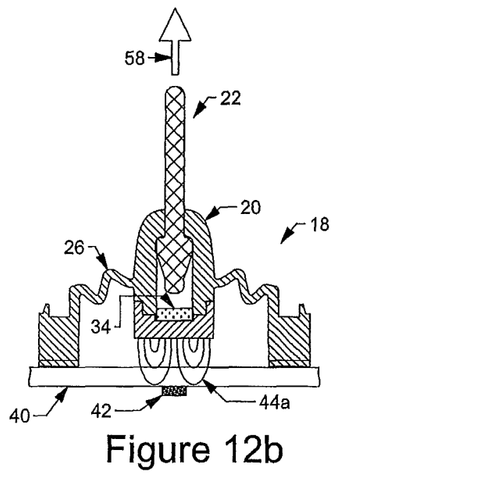
FIG. 12b is a second cross-sectional view of the plate portion and pull-cord coupler of FIG. 10 in an intermediate, or distorted, position with magnetic field lines.

Referring to FIGS. 12a and 12b, the pull-cord sensor assembly 10 can be seen as being in an activation position. This activation position can be seen as a straight activation position as there may be many different activation positions for the sensor assembly of the present disclosure. In this embodiment, the pull cord is pulled in the direction represented by arrow 58 whereby the plate portion 18 is subject to distortion due to the pull of the pull cord. In the current example, the force applied to the plate portion 18 can be seen as essentially perpendicular to the plane of substrate 40. It will be understood that the magnitude of the distortion is partially determined by the flexibility of the plate portion 18, the thickness and geometry of annular rings 26 and the applied force. The application of force causes the distance between the magnet 34 and the sensor 42 to increase resulting in the sensor sensing a magnetic field strength of lower magnitude than in the rest position of FIGS. 11a and 11b. Therefore, with an applied force of sufficient magnitude to change the sensed magnetic field strength, providing it is lower than a predetermined threshold, the magnetic sensor generates a detection signal to activate the necessary alarm or signal. As outlined above, this may be performed by causing a change of state of the detection signal, or change in the proportional output, of magnetic sensor 42.

Figure 13A:
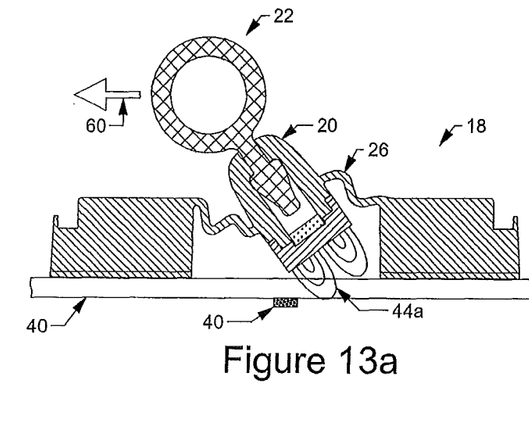
FIG. 13a is a cross-sectional view of the plate portion and pull-cord coupler of FIG. 10 in a diagonal position with magnetic field lines.
Figure 13B:
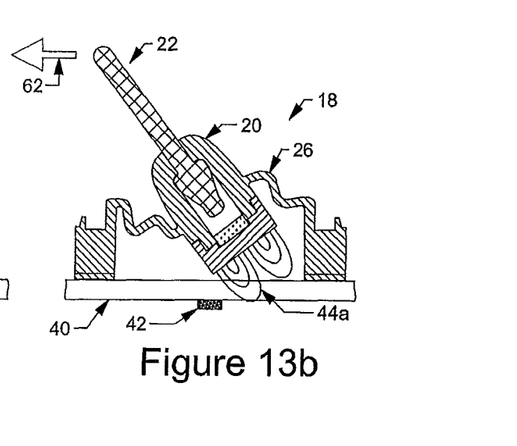
FIG. 13b is a second cross-sectional view of the plate portion and pull-cord coupler of FIG. 10 in a diagonal position with magnetic field lines.

Referring now to FIGS. 13a and 13b, schematic diagrams of the pull-cord sensor assembly 10 in another activation position is shown. This activation position may be seen as a diagonal activation position. In the current embodiment (as shown in FIGS. 13a and 13b), the pull-cord sensor assembly 10 (or plate portion 18) is subject to distortion due to forces, represented by arrows 60 and 62, respectively, applied essentially parallel to the plane of substrate 40. As above, the magnitude of the distortion is determined by the flexibility of plate portion 18, the thickness and geometry of annular rings 26 and the applied forces 60 and 62. In the current embodiment, the force represented by arrow 60 and the force represented by arrow 62 are applied substantially perpendicular to each other, but the distortions of the pull-cord sensor assembly 10 resulting from the applied forces are substantially equivalent. It will be understood that any force applied in any direction substantially parallel to the plane of substrate 40 results in an equivalent or similar distortion of the plate portion of pull-cord sensor assembly 10.

As can be seen, as the pull-cord sensor assembly is moved, the distance between the magnet 34 and the sensor 42 increases. The direction of the magnetic field generated by the magnet also changes (such as schematically shown in FIGS. 13a and 13b). It will be further understood that as the magnetic field of magnet 34 is strongest on the center axis of magnet 34, and conversely weaker elsewhere, the magnetic field being exposed to the sensor 42 is a progressively weaker magnetic field with increased degree of distortion or movement of the magnet 34 away from the sensor 42. It will also be understood that distortion of pull-cord sensor assembly 10 changes the angle of magnetic lines 44a with respect to magnetic sensor 42, and as outlined above, since magnetic sensor 42 is preferably sensitive to magnetic fields perpendicular to its mounting axis, the change in angle of magnetic lines 44a results in a lower sensed magnetic field strength consequently, with an applied force of sufficient magnitude, a detection signal is generated either by changing a state of the detection signal, or a change of proportional output, of magnetic sensor 42.

Although two examples of forces being applied to the pull-cord assembly are shown in FIGS. 12 and 13, a force applied to the pull-cord at any angle between parallel and perpendicular to the plane of substrate 40 results in a distortion of pull-cord sensor assembly 10 (or plate portion) that increases the distance between magnet 34 and magnetic sensor 42 and/or changes the angle of magnetic lines 44a with respect to magnetic sensor 42. This results in the magnetic sensor 42 being exposed to a weaker magnetic field of magnet 34, that may, and likely will, cause the magnetic field being sensed by the sensor to change thereby causing a detection signal to be generated.

It will be understood that any force of sufficient magnitude applied to the activation portion applied on any radial of the center axis of pull-cord sensor assembly 10 at any positive elevation relative to the plane of substrate 40 will likely result in a change of state of the detection signal, or change of proportional output in excess of the predetermined threshold of magnetic sensor 42.

Figure 14:
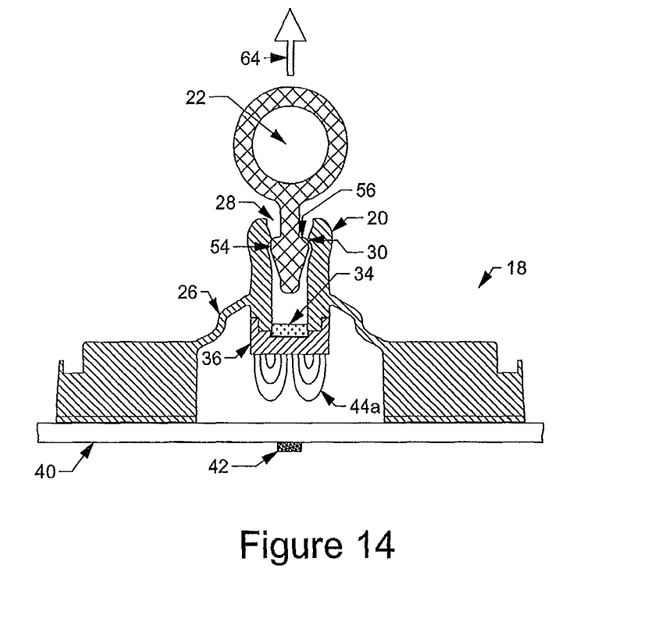
FIG. 14 is a cross-sectional view of the plate portion and pull-cord coupler of FIG. 10 in an extended position with magnetic field lines.

Turning to FIG. 14, a break-away aspect of one embodiment of a pull-cord sensor assembly is shown. When a force, represented by arrow 64, is applied to pull-cord coupler 222 that causes the annular rings 26 to flex beyond their limits of their extension due to increased forces exerted by edge 56 on annular ridge 30, the diameter of hole 28 is increased. As mentioned above, this relates to the embodiment where the plate portion 18 is made of an elastomeric material. It will be understood that, with increasing applied force, the diameter of hole 28 increases until rib 54 passes through the enlarged opening of annular ridge 30 and, with a consequent reduction or elimination of the force applied by annular ridge 30 to edge 56, annular rings 26 may return central portion 20 to its resting position, leaving pull-cord coupler detached therefrom. In an alternative embodiment, the annular rings 26 may keep the central portion 20 in an extended position.

It will be further understood that the magnitude of force sufficient to withdraw the pull-cord coupler 22 from the central portion is determined by the flexibility of plate portion 18, the diameter of hole 28, the diameter of rib 54 and the radius between rib 54 and edge or surface 56. Furthermore, it will be understood that any force of sufficient magnitude applied to the pull-cord coupler on any radial of the center axis of pull-cord sensor assembly 10 at any positive elevation relative to the plane of substrate 40 may result in similar distortion of pull-cord sensor assembly 10 resulting in the extraction of pull-cord coupler 22 from central portion 20.

Figure 15:
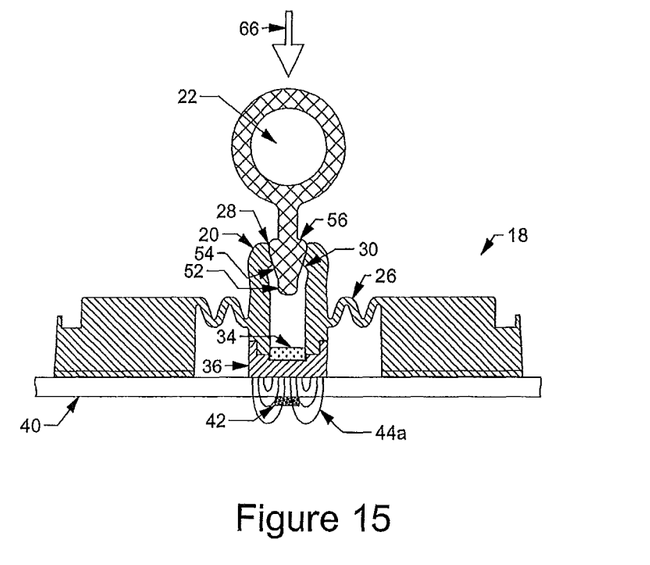
FIG. 15 is a cross-sectional view of the plate portion and pull-cord coupler of FIG. 10 with the pull-cord coupler in an initially inserted position.

Referring now to FIG. 15, when a force, represented by arrow 66, is applied to pull-cord coupler essentially perpendicular to the plane of substrate 40, a radial force is exerted by ramp 52 that tends to increase the diameter of hole 28. It will be understood that, with increasing applied force, the diameter of hole 28 diameter increases until rib 54 passes completely through the enlarged opening of annular ridge 30. It will be further understood that the magnitude of the force sufficient to insert pull-cord coupler 22 fully into pull-cord sensor assembly 10 is determined by the flexibility of the plate portion 18, the diameter of hole 28, the diameter of rib 54 and the slope of ramp 52 and surface friction between the two parts.

Figure 16A:
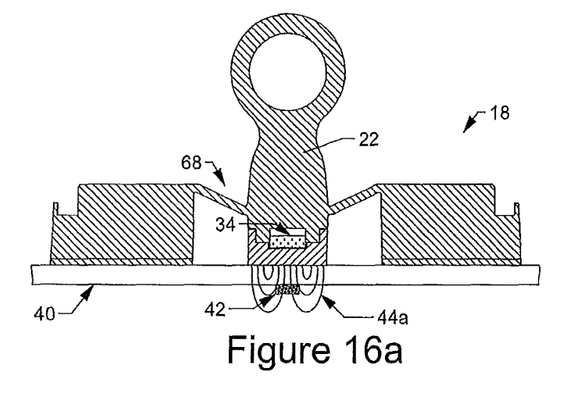
FIG. 16a is a cross-sectional view of another embodiment of a plate portion and pull-cord coupler.
Figure 16B:
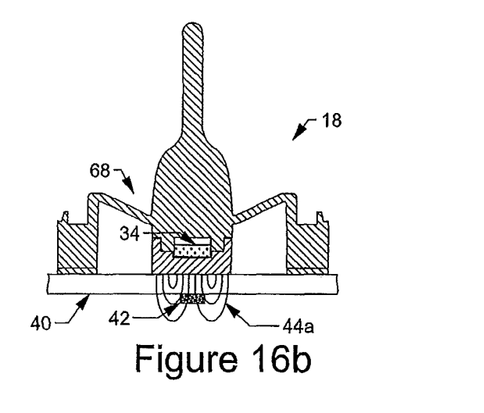

Turning to FIGS. 16a and 16b, further cross-sectional views of another embodiment of a pull-cord sensor assembly are shown. In the embodiment of FIGS. 16a and 16b, the activation portion (or attachment mechanism) 22 and the central portion 20 can be seen as a single piece whereby the pull-cord (not shown) can be connected to the attachment mechanism. In this embodiment, there is no break-away system within the plate portion 18, however, a break-away system may be implemented within the pull-cord. In the current embodiment, the coupler 22 and central portion 20 may be permanently affixed to the plate portion 18 via connectors or connecting elements 68. Operation of this embodiment (to determine when a detection signal should be generated) will be the same as described above with respect to the previous embodiment.

Figure 17A:
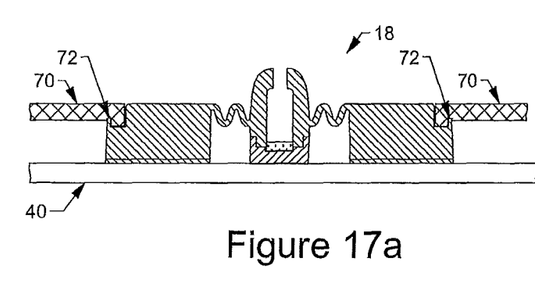
FIG. 17a is a cross-sectional view of yet another embodiment of a plate portion and pull-cord coupler.
Figure 17B:
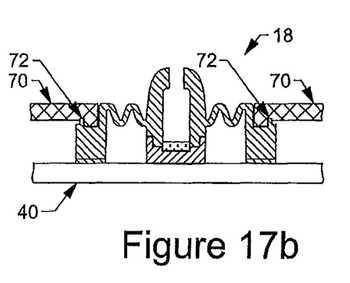

Turning to FIGS. 17a and 17b, a further embodiment of a pull-cord sensor assembly is shown. In the current embodiment, the pull-cord sensor assembly is integrated with a front plate 70, such as a cover of the call station. As can be seen, the plate portion 18 includes the ridge or rib 72 that secures the plate portion 18 to the front plate 70 whereby a water-tight seal may be enabled via the compression of the rib by the plate.

Figure 18:
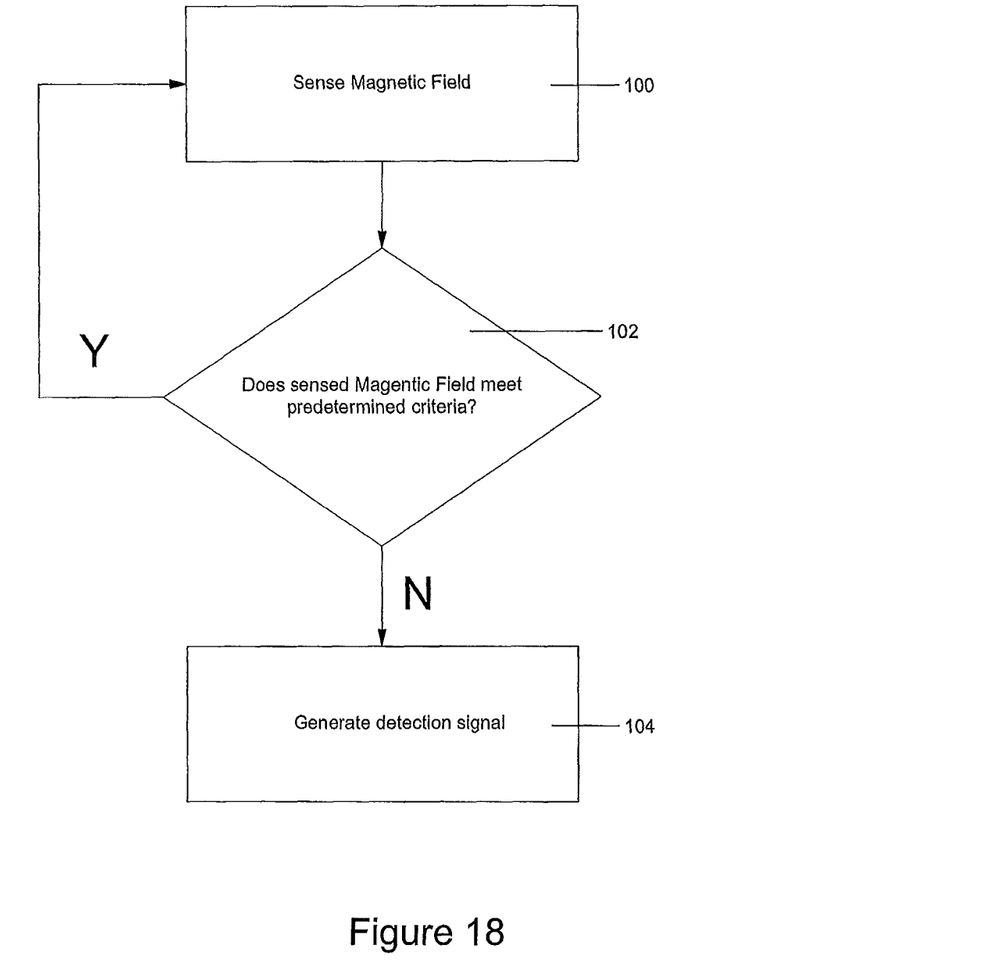
FIG. 18 is a flowchart outlining a method of triggering an alarm for a pull-cord sensor assembly.

Turning to FIG. 18, a flowchart outlining a method of generating a detection signal is shown. Initially, a magnetic field is sensed 100. A check is then performed to determine if the sensed magnetic field is meets predetermined criteria such as being less than, equal to or greater than a threshold value 102. If the sensed magnetic field meets the criteria, the magnetic field continues to be sensed. If the sensed magnetic field does not meet the predetermined criteria, a detection signal is generated 104. In one embodiment, a sensor may transmit a signal to a processor to generate an alarm. In another embodiment, the sensor may generate an output proportionate to the magnetic field being sensed which serves as a detection signal for the system to generate the necessary alarm or warning.

It will be understood that in one embodiment, the pull-cord can include a breakaway apparatus such that the pull-cord can be "broken away" or separated from the central portion, however, in other embodiments, the plate portion may include apparatus for keeping the activation portion inserted within the central portion. In another embodiment, the call station may include lights that turn on when the detection signal is generated (such as when the pull-cord is activated). In a further embodiment, the call station may include audible alarms when the detection signal is generated or the pull-cord is activated.

It will be appreciated by those skilled in the art that the invention can take many forms, and that such forms are within the scope of the invention as described above. The foregoing descriptions are exemplary, and their scope should not be limited to the preferred versions contained herein.

What is claimed is:

1. A pull-cord sensor assembly comprising:
   an activation portion including a magnet configured to generate a magnetic field;
   a sensor configured to sense a level of the magnetic field of the magnet;
   a comparator connected to the sensor and configured to compare the sensed level of the magnetic field with a threshold value to determine if the sensed level meets the threshold value; and
   a pull cord operatively connected with the activation portion;
   wherein the pull cord can be pulled in any three-dimensional direction from where the pull cord is integrated with the activation portion
   wherein the activation portion further includes:
      a pull-cord coupler including:
         a tip portion;
         a rib portion;
         a ramp portion connecting the tip portion to the rib portion whereby a diameter of the trip portion is less than a diameter of the rib portion; and
         a ring portion connected to the rib portion; and
      a plate portion having a central portion, the central portion integrated with the pull-cord coupler.

2. The sensor assembly of claim 1 wherein the pull-cord coupler and the plate portion are a single piece.

3. The sensor assembly of claim 1 wherein the pull-cord is integrated with the activation portion via the ring portion.

4. The sensor assembly of claim 1 wherein the central portion comprises:
   an annular housing portion defined by an annular wall for housing the pull-cord coupler; and
   an opening at one end of the central portion for receiving the pull-cord coupler;
   wherein a diameter of the opening is smaller than a diameter of the annular housing and
   wherein the magnet is located at an end of the central portion opposite the opening.

5. The sensor assembly of claim 4 wherein the annular housing portion includes an annular ridge.

6. The sensor assembly of claim 1 further comprising a substrate portion wherein the activation portion is mounted on one side of the substrate portion and the sensor is mounted on another side of the substrate opposite the activation portion.

7. The sensor assembly of claim 6 wherein the sensor is mounted directly opposite the magnet portion.

8. The sensor assembly of claim 6 wherein the substrate portion is a printed circuit board.

9. The sensor assembly of claim 6 wherein the sensor is mounted adjacent the magnet portion.

10. The sensor assembly of claim 9 wherein the plate portion is made from an elastomeric material.

11. The sensor assembly of claim 9 wherein the pull cord comprises a handle at an end of the pull cord opposite the activation portion.

12. The sensor assembly of claim 9 wherein the comparator is a processor or an electronic circuit.

13. The sensor assembly of claim 12 wherein the comparator is integrated with the sensor.

14. A pull-cord sensor assembly comprising:
   an activation portion including a magnet configured to generate a magnetic field;
   a sensor configured to sense a level of the magnetic field of the magnet;
   a comparator connected to the sensor and configured to compare the sensed level of the magnetic field with a threshold value to determine if the sensed level meets the threshold value; and
   a pull cord operatively connected with the activation portion;
   wherein the pull cord can be pulled in any three-dimensional direction from where the pull cord is integrated with the activation portion
   wherein the activation portion further includes:
      a pull-cord coupler; and
      a plate portion having a central portion, the central portion integrated with the pull-cord coupler, and at least one annular ring surrounding the central portion enabling flexibility of the central portion.

15. The sensor assembly of claim 14 further comprising a substrate portion wherein the activation portion is mounted on one side of the substrate portion and the sensor is mounted on another side of the substrate opposite the activation portion.

16. The sensor assembly of claim 15 wherein the sensor is mounted directly opposite the magnet portion.

17. The sensor assembly of claim 15 wherein the substrate portion is a printed circuit board.

18. The sensor assembly of claim 15 wherein the sensor is mounted adjacent the magnet portion.

19. The sensor assembly of claim 14 wherein the plate portion is made from an elastomeric material.

20. The sensor assembly of claim 14 wherein the comparator is a processor or an electronic circuit.

* * * * *